United States Patent
Ferguson et al.

(10) Patent No.: US 6,855,505 B2
(45) Date of Patent: Feb. 15, 2005

(54) METHOD FOR QUANTIFYING TGF-β

(75) Inventors: Mark W. J. Ferguson, Derbyshire (GB); Georg Brunner, Munster (DE)

(73) Assignee: Renovo Limited, Manchester (GB)

(*) Notice: Subject to any disclaimer, the term of this patent is extended or adjusted under 35 U.S.C. 154(b) by 37 days.

(21) Appl. No.: 10/291,755

(22) Filed: Nov. 12, 2002

(65) Prior Publication Data

US 2003/0129668 A1 Jul. 10, 2003

Related U.S. Application Data

(63) Continuation of application No. 09/720,359, filed as application No. PCT/GB99/01998 on Jun. 25, 1999, now abandoned.

(30) Foreign Application Priority Data

Jun. 26, 1998 (GB) ............................................. 9813715

(51) Int. Cl.[7] ......................... G01N 33/53; C07K 14/00
(52) U.S. Cl. ...................... 435/7.1; 435/7.95; 530/399
(58) Field of Search ............................... 435/7.1, 7.95; 530/399

(56) References Cited

FOREIGN PATENT DOCUMENTS

WO          95/19987          7/1995

OTHER PUBLICATIONS

Abe M et al.: "An Assay for Transforming Growth Factor–Using Cells Transfected with a Plasminogen Activator Inhibitor–1 Promoter–Luciferase Construct" Analytical Biochemistry, vol. 216, No. 2, 2/1994, pp. 276–284.

Shah M et al.: "Control of Scarring in Adult Wounds by Neutralising Antibody to Transforming Growth Factor Beta" Lancet The, vol. 339, Jan. 1992, pp. 213/214.

Yang, Liju et al.: "Active transforming growth factor–beta. in wound repair: determination using a new assay" Am. J. Pathol., 154(1), 105–111 Jan. 1999.

Blewett et al, "Regenerative Healing of Incisional Wounds in Murine Fetal Lungs Maintained in Organ Culture", J. Pediatric Surgery 30(7):945–948 (1995).

Barcellos–Hoff et al, "Immunohistochemical Detection of Active Transforming Growth Factor–β in Situ Using Engineered Tissue", American J. Pathology 147:1228–1237 (1995).

*Primary Examiner*—Janet Andres
(74) *Attorney, Agent, or Firm*—Nixon & Vanderhye P.C.

(57) ABSTRACT

The present invention relates to a method for quantifying the amount of active transforming growth factor beta (TGF-β) in biological samples. In particular the method comprising incubating cryosections of a tissue with cells which contain a TGF-β responsive expression vector having a structural region encoding an indicator protein and measuring the amount of said indicator protein expressed from the cells.

18 Claims, 7 Drawing Sheets

METHOD FOR QUANTIFYING TGF-β

This application is a continuation of application Ser. No. 09/720,359, filed Jan. 22, 2001, now abandoned, which is a 371 of PCT/GB99/01998, filed Jun. 25, 1999, the entire content of which is hereby incorporated by reference in this application.

The present invention relates to methods for quantifying the amount of active transforming growth factor beta (TGF-β) in biological samples.

The TGF-β family of growth factors are potent regulators of cell growth and differentiation. TGF-βs are known to be expressed throughout embryogenesis and are detected at high levels in areas undergoing rapid morphogenesis suggesting an important role in development, tissue repair and regeneration. TGF-βs exist in a number of structurally related but functionally distinct 25-kDa homodimeric isoforms. In mammals, three isoforms, TGF-β1, 2 and 3 have been identified. Each isoform is synthesised as a large latent precursor which is unable to trigger signalling via high-affinity TGF-β receptors. Therefore, activation of latent TGF-β isoforms appears to be a critical control point in regulating their biological activity.

In vitro latent TGF-βs can be activated by a variety of treatments such as incubation at extremes of pH, at high temperature, with proteases or by interaction with thrombospondin. Evidence suggests that limited proteolysis by plasmin may be involved in the physiological activation of latent TGF-β. However, the mechanisms of latent TGF-β activation in vivo remain unknown.

A large body of evidence has suggested that TGF-β has profound effects on wound repair. Wound healing is a highly regulated process involving inflammation, cell proliferation and migration, angiogenesis, and extracellular matrix (ECM) production. TGF-βs regulate most of these events including the chemotaxis of inflammatory cells, angiogenesis, ECM deposition and granulation tissue formation, thereby promoting healing and contributing to scar formation. TGF-β1 has also been implicated in abnormal wound healing, such as hypertrophic scar and keloid formation as well as in fibrotic diseases, such as glomerulonephritis, liver cirrhosis, and pulmonary fibrosis. Exogenous addition of TGF-β1 or TGF-β2 has been shown to accelerate wound healing of chronic wounds or other situations of impaired wound repair. The TGF-β isoforms have distinct biological activities in regulating wound repair. The manipulation of the ratio of TGF-β isoforms in adult rat wounds, particularly reducing the level of TGF-β1 and TGF-β2 relative to TGF-β3 reduces scarring. By contrast, exogenous addition of TGF-β1 to foetal rabbit or mouse wounds, which normally heal without a scar, induces scar formation.

TGF-β and TGF-β receptors are expressed ubiquitously in the body. Since the activation of the latent form of TGF-β is a critical step in the regulation of the bioactivity of this growth factor, modulation of latent TGF-β activation in vivo might be a promising approach to modulate TGF action, e.g. in wound repair and scarring. However, although the potent effects of TGF-β isoforms in wound repair have been clearly demonstrated, it has so far not been technically possible, due to the lack of a quantitative assay for active TGF-β isoforms in vivo, to monitor latent TGF-β activation at the wound site.

In most biological systems active TGF-β is present in picogram amounts. These low concentrations, however, are sufficient to induce a variety of biological responses such as macrophage chemotaxis, inhibition of endothelial cell migration and proliferation, inhibition of mink lung epithelial cell (MLEC) proliferation, stimulation of ECM deposition and decreased plasminogen activator activity as a result of decreased plasminogen activator production and increased secretion of its inhibitor, plasminogen activator inhibitor-1 (PAI-1). These and other biological effects of TGF-β activity have been used to develop a variety of quantitative bioassays, including those based on chondrogenesis, inhibition of DNA synthesis and cell growth, differentiation, migration or plasminogen activator activity. Many of these assays are complicated to establish and can be influenced by other factors present in the biological samples under assay, such as growth factors including basic fibroblast growth factor, epidermal growth factor and platelet-derived growth factor and insulin, making the assay results difficult to interpret. For example proteases present in biological samples may cleave latent TGF-β to active TGF-β and therefore assays on biological samples could provide misleading results when used as an indication of active TGF-β levels in vivo.

Specific assays for active TGF-β include the radioreceptor, radioimmunoassay (RIA) and the enzyme-linked immunosorbent assay (ELISA). Radioreceptor assays using a variety of cell types have been described and have ranges of 125 pg/ml to 25 ng/ml. The affinities of different antibodies used can greatly alter the sensitivity of the assay.

Isoform-specific double antibody or sandwich ELISAa (SELISA) are also very sensitive to the affinities of the antibodies. One such assay, using two different monoclonal antibodies specific for active TGF-β1, had a useful range of 0.63 to 40 ng/ml (Lucas et al., In Peptide Growth Factors, Barnes et al., Eds, Academic Press Inc. 198: 303–316, 1991). Although highly sensitive and specific, SELISAs such as these are not readily available and are relatively expensive.

Although known TGF-β assays can detect active TGF-β in vitro, the low concentrations (less than 2 pM) generated in various biological systems make many of then impractical without prior concentration of the sample. This can result in large losses of the active growth factor or more importantly activation of latent TGF-β. Moreover, many of the known assays are complicated to establish and can be influenced by other factors present in the sample thus reducing their utility for accurately measuring the amount of active TGF-β in an in vivo sample.

A known assay for the quantification of active TGF-β (Abe et al., "An assay for transforming growth factor-β using cells transfected with a plasminogen activator inhibitor-1 promoter luciferase construct" Anal Biochem, 216:276–284, 1994) has been used for assaying TGF-β levels in vitro in biological solutions. The assay relies on the ability of TGF-β to stimulate PAI-1 and utilises a TGF-β responsive cell containing an expression vector having a TGF-β response element (the PAI-1 promoter) and a structural region encoding an indicator molecule, for example luciferase. TGF-β present in a test sample induces activation of the PAI-1 promoter. This results in transcription and the expression of the indicator molecule. Measurement of the amount of indicator molecule determines the amount of TGF-β responsible for the induced activation. This assay provides a method of quantifying the amount of TGF-β in a body fluid, in culture medium and in lysed tissue extract at concentrations of 0.2 to 30 pM. All of the samples analysed using this assay are in vitro liquid samples. Abe et al., 1994, supra, does not disclose the use of the assay on solid samples or whole cells.

It is therefore an object of the present invention to obviate or mitigate the abovementioned disadvantages of previously known assays for TGF-β levels.

According to the present invention there is provided an assay method for quantifying the amount of active transforming growth factor β (TGF-β) in a sample, comprising:

(a) incubating the sample together with eukaryotic cells which contain a TGF-β responsive expression vector having a structural region encoding an indicator protein for a predetermined time period sufficient for said eukaryotic cells to express a detectable amount of said indicator protein;
(b) measuring the amount of said indicator protein expressed during said time period; and
(c) determining the amount of TGF-β present in the sample by comparing the measured amount of said indicator protein against reference data; characterised in that the sample comprises a cryosection of a tissue.

The assay method is based on the ability of TGF-β to induce plasminogen activator inhibitor-1 (PAI-1) expression and is a modification of the PAI-1 luciferase assay of Abe et al., 1994, supra which is also disclosed in WO 95/19987 (Lockutoff and Curriden), both of said disclosures are incorporated herein by reference. The known PAI-L assay uses a truncated TGF-β inducible PAI-1 promoter fused to a firefly luciferase reporter gene in a vector to transfect mink lung epithelial cells (MLECs) to generate a highly sensitive TGF-β-responsive cell line which may also be utilised in accordance with the present invention. The known PAI-1 assay is used to measure TGF-β levels in liquid sample whereas the present invention utilises the same or a similar assay on a cryosection to give a clearer reflection of events in vivo. All of the features of the assay according to the present invention, other than the sample type used, may be as disclosed in Abe et al., 1994, supra, and in WO 95/19987.

The inventors recognised a problem associated with the known PAI-1 luciferase assay of Abe et al., 1994, supra, in that only liquid samples were used in the assay. The results of the known assay only give levels of TGF-β in vitro, whereas it is desirable to have an indication of the TGF-β levels in vivo to study activation of TGF-β in vivo in response to stimuli, such as may occur during wound healing.

The inventors found that when the known PAI-L assay was used on lysed cell extracts it did not provide an accurate reflection of the amount of active TGF-β present in vivo. We believe the problem was that when the cells of the extract were lysed they released agents such as proteases and growth factors. The various members of the TGF-β family are known to have various forms—free TGF-β is the active form which is assayed for using the PAI-L assay. However in vivo TGF-β is also present as the TGF-β-LAP (TGF-β-Latency Associated Peptide) complex and the TGF-β-LAP-latent TGF-β binding protein complex (LTBP). By lysing the cells the various levels of each of the forms of TGF-β may be altered such that the assay on the lysed cell extract does not provide a clear reflection of TGF-β levels in vivo.

Having recognised the problem that agents released from cells in a sample may affect TGF-β levels, we realised tissue cryosections maybe used as the samples in the known assay of Abe et al., 1994, supra.

One of the reasons that only liquid samples were used in the assay of Abe et al., 1994, supra was probably because the volume of a liquid sample under test is simple to measure and therefore the concentration of active TGF-β in that sample easily determinable, (once the amount of active TGF-β was determined by the assay). It is more difficult to determine the actual volume of a solid sample under test, for example a cube of tissue, as the assay may not necessarily penetrate through the whole of the solid sample. Therefore, even if the assay of Abe et al., 1994, supra was used to assay the concentration of active TGF-β in a solid sample, the assay results may not have given a true indication of the actual in vivo active TGF-β level in that sample due to the difficulty in accurately determining the volume of that solid sample.

The inventors have been able to determine the volume of the cryosections used as their samples. Therefore, the inventors have been able to utilise cryosections in an assay for TGF-β levels previously only carried out on liquid samples. The use of cryosections in the assay allows for semi-quantitative determination of TGF-β levels in vivo, the assay result providing an accurate reflection of events in the tissue. The assay will have utility in monitoring latent TGF-β activation in a system that reflects in vivo conditions, allowing proposed modulators of TGF-β activation to be tested with some degree of accuracy. TGF-β present in tissues may be an important prognostic and therapeutic marker in certain conditions. Therefore, being able to effectively measure the likely levels of active TGF-β isoforms in a particular tissue by the assay described herein may contribute to improved strategies for prognosis and/or post-operative treatment for pathological conditions in which TGF-β plays important roles, for example wound repair, fibrosis and cancer development.

The eukaryotic cells containing a TGF-β responsive expression vector having a structural region encoding an indicator protein may be the MLECs described in Abe et al., 1994, supra, and in WO 95/19987. Preferably, the indicator protein is luciferase. Luciferase expression, activated by TGF-β may be determined using a luminometer, preferably an MLX Microtiter Plate Luminometer as produced by Dynex Technologies of Chantilly, Va., USA.

The cryosections for use in the assay method according to the present invention may be prepared by dissecting extracts of tissue and embedding them in methyl cellulose or a similar support before snap freezing the tissue in liquid nitrogen. The embedded tissue samples may be stored at −80° C. preferably for a maximum of three months. Cryosections of up to 50 μm thick, preferably of less than 30 μm thick and more preferably 20 μm thick may be used in the assay method according to the present invention. The cryosections are preferably mounted on coverslips, preferably, sterilised round coverslips. Each coverslip may carry more than one cryosection and preferably, up to four cryosections are present on a single coverslip.

The area of each cryosection sample may be determined by staining and imaging. Staining may be by haematoxylin and eosin. The volume of the cryosection may be determined from the area of the cryosection and its thickness.

To carry out the method according to the present invention, the cryosections are incubated with the eukaryotic cells containing a TGF-β responsive vector.

Preferably, the incubation is by inverting a coverslip carrying one or more cryosections and placing the coverslip over the eukaryotic cell culture such that each cryosection contacts the eukaryotic cells. Alternatively, the cryosections may be placed in a tissue culture well, face up and the indicator cells added to the well to cover the cryosection.

The method according to the present invention may be carried out on both test samples and control samples to evaluate TGF-β levels in vivo. For example, a test sample may comprise an agent which putatively activates latent TGF-β and the control sample may comprise cells without the agent added. The TGF-β activity in test and control samples may then be compared to assess the effect of the agent on TGF-β activity.

The reference data for TGF-β activity may be prepared by adding serial dilutions of a TGF-β of known concentrations (preferably human recombinant TGF-β) to the eukaryotic cells together with the cryosection free coverslip.

The assay method according to the present invention may also be used to determine the ratios of active TGF-β isoforms in the cryosections to provide an indication of the ratios of active TGF-β isoforms in vivo.

To measure the ratios of active TGF-β isoforms in a cryosection the assay method according to the present invention may be preceded by the step of preincubating the cryosections with anti-TGF-β isoform neutralising antibodies, such as anti-TGF-β1, 2 and 3, preferably at a concentration of 1–5 μg/ml for a predetermined length of time, preferably about one hour, preferably at room temperature before transferring the cryosections to be incubated with the eukaryotic cells in the assay method according to the present invention. Suitable controls include non-immune chicken immunoglobulin Y and non-immune goat immunoglobulin G (for the preferred anti-TGF-β antibodies described herein). It will be appreciated when different antibodies (i.e. primary antibodies) are used then appropriate species and chain specific central antibodies should be used.

Determination of the levels of different TGF-β isoforms in the cryosection provides an indication of the ratio of these isoforms in vivo. Using the assay of the present invention in this way will make it possible to monitor the progression of disease states or wound healing, for example, where the different TGF-β isoforms have been shown to have distinct functions. For instance the assay may be used as a basis for the discovery of agents which reduce the levels of active TGF-$β_1$/TGF-$β_2$ compared to the levels of TGF-$β_3$ and which may therefore be effective anti scarring/anti fibrotic agents. The method according to the invention provides a means of validating/optimising putative anti-TGF-β or pro-TGF-β therapeutic approaches. It could also be used to discover molecules which enhance the levels of active TGF-β (important in accelerating wound healing) as well as reducing the levels of active TGF-$β_1$/TGF-$β_2$ (antiscarring/ antifibrotic) or for altering the ratio of active TGF-$β_1$/TGF-$β_2$:TGF-$β_3$ (antiscarring). The method may also be used to discover the importance of active TGF-β in disease processes and hence in the development of new therapies. Furthermore, the method according to the invention may be used as a diagnostic test to evaluate levels of active TGF-β in a tissue (e.g. diseased or wounded tissues) and hence allow a physician to select an effective therapy.

The method according to the present invention may be used, if preceded by a heat activation step, to measure the total TGF-β levels in a cryosection sample. The method according to the present invention measures only active TGF-β levels in the sample. TGF-β may also be present in the sample in its latent form, associated with other proteins such as LAP or LTBP. Heat activation of the cryosection breaks down the majority of the latent TGF-β in the sample into active TGF-β which can be assayed as previously. Preferably heat activation comprises heating the cryosections to about 80° C. for 20 minutes.

By carrying out the assay method according to the present invention first on standard cryosections and then on heat treated cryosections the ratio of active to total TGF-β in the cryosection may be determined, thus providing the ratio of active to latent TGF-β in that cryosection. Determination of the ratio of active to latent TGF-β in the cryosection allows the ratio to be followed in response to stimuli to determine any changes in the active to latent TGF-β ratio during, for example, wound healing, or as part of disease progression. Monitoring the ratio in cryosections provides an accurate reflection of TGF-β levels in vivo. Assays already known to the art have previously been unsuitable for accurately measuring in vivo activity because of the artificial changes to TGF-β activity induced by proteases etc.

The invention will be further described by way of example only with reference to the accompanying drawings in which:

As shown in FIG. 1A MLECs (10) were plated for 4 h into 24-well plates, one well (12) being represented in FIG. 1A ($3 \times 10^5$/ml, 500 μl/well) in complete DMEM and incubated for 4 hours at 37° C. Then, serum-containing medium was replaced with 500 μl of DMEM containing 0.1% pyrogen-poor BSA, aprotinin (1 μg/ml), penicillin (100 U/ml) and streptomycin (100 μg/ml), designated DMEM-BAS medium (14). The coverslips (16) carrying cryosections (18) were placed upside down onto the MLECs (10) in the 24-well plates. As shown in FIG. 1B, to generate a TGF-β standard curve, MLECs (10) were incubated with serial dilutions of recombinant human TGF-β1 (0–250 pg/ml) in DMEM-BSA medium (20). These serial dilutions were added to the MLECs (10) together with methyl-cellulose coated coverslips (16). Both samples and TGF-β standards were incubated with the MLECs (10) overnight at 37° C. MLECs (10) were then washed with phosphate buffered saline (PBS) and lysed with 200 μl of luciferase cell lysis buffer for 20 minutes at room temperature. Forty-five microliters of the lysates was transferred in triplicate to a Microlite 96-well plate. Luciferase activity in the lysates was determined using an MLX Microtiter Plate Luminometer.

EXAMPLES

General Methodology

The method in accordance with the present invention is illustrated by its use in determining the levels of active TGF-β in cryosections taken from wound tissue.

Dermal Wound Healing Model

Adult male Sprague-Dawley rats (Charles River UK Ltd, Kent, UK) weighing 225–250 g were anaesthetised by inhalation of halothane, nitrous oxide, and oxygen. The back of the rats was shaved, and four full-thickness linear incisions of 1 cm length, including the panniculus carnosus, were made on the back of the animals using a scalpel as described in Shah et al., "Control of scarring in adult wounds by neutralising antibody to transforming growth factor β, Lancet. 339: 213–214, 1992. The wounds were left unsutured to heal by secondary intention. The animals were allowed to recover, housed separately, and fed ad libitum until the wounds were harvested. The animals were killed by chloroform overdose at 1 hour, 6 hour, or 1, 2, 3, 4, 5, 7, 10 and 14 days post-wounding. The wounds were harvested and processed as described below. All animal experiments were carried out under appropriate licences according to UK Home Office regulations.

Preparation of Cryosections

The wound area was swabbed with 70% ethanol. The wounds were carefully dissected from surrounding tissue and subsequently embedded in 8% sterile methyl cellulose (Sigma, Dorset, UK) and snap frozen in liquid nitrogen. Four wounds from each animal were embedded in one block of methyl cellulose. Four tissue samples of equivalent size representing surrounding tissue adjacent to the wound were also excised and processed as described above. Normal skin from the back of non-wounded rats was used as a control. The embedded tissue samples were stored at −80° C. for a maximum of 3 months. Thick cryosections (20 μm) were cut and placed on sterilised 13-mm round coverslips and analysed in duplicate. The coverslips, each carrying 4 cryosections of the wound, were placed into a 24-well cell culture plate and temporarily stored at −20° C. until transferred onto mink lung epithelial cells (MLECs).

In order to measure the volume of the tissue sections, serial cryosections from the same specimen were stained with haematoxylin and eosin (HE). Colour images of HE-stained wound sections were captured using a colour video camera (3-CCD JVC KY-F55) connected to an Olympus Vanox AHBS3 microscope. The image capturing process employed a Spynt Capture Board (Synoptics) in a Dan 486 66 MHz computer running PC Image (Foster Findlay) in Windows 3.11. The area of the wound was measured using the stylus of a digitising tablet (Summgraphics, summesketch III). The volume of the wound was calculated from the area of the wound and the thickness of the section.

Cell Culture

Mink lung epithelial cells (MLECs) transfected with the PAI/L construct were a generous gift from Dr. Daniel B. Rifkin (New York University Medical Center, USA) and were the same as those disclosed in WO 95/19987 (Lockutoff & Curriden). MLECs were cultured in Dulbecco's modified Eagle's medium (DMEM) supplemented with 5% foetal calf serum (FCS), L-glutamine (2 mM), penicillin (100 U/ml) and streptomycin (100 μg/ml) (all purchased from Gibco BRL, Paisley, UK) and geneticin (G418) (250 μg/ml) purchased from Sigma, Dorset UK. Cells were used between passage 8 and 20.

Example 1

Determination of Active/Latent TGF-β in the PAI/L Assay

For the PAI/L assay, a truncated TGF-β-inducible PAI-1 promoter has been fused to a firefly luciferase reporter gene and subsequently transfected into MLECs generating a highly sensitive TGF-β-responsive cell line (Abe et al, 1994 and WO 95/19987 supra). The PAI/L assay is specific for active TGF-β1, 2, or 3, and the detection limit is approximately 10 pg/ml. This assay has been used previously for the quantification of active TGF-β in conditioned medium, blood samples, or other liquid samples.

Figure 1:
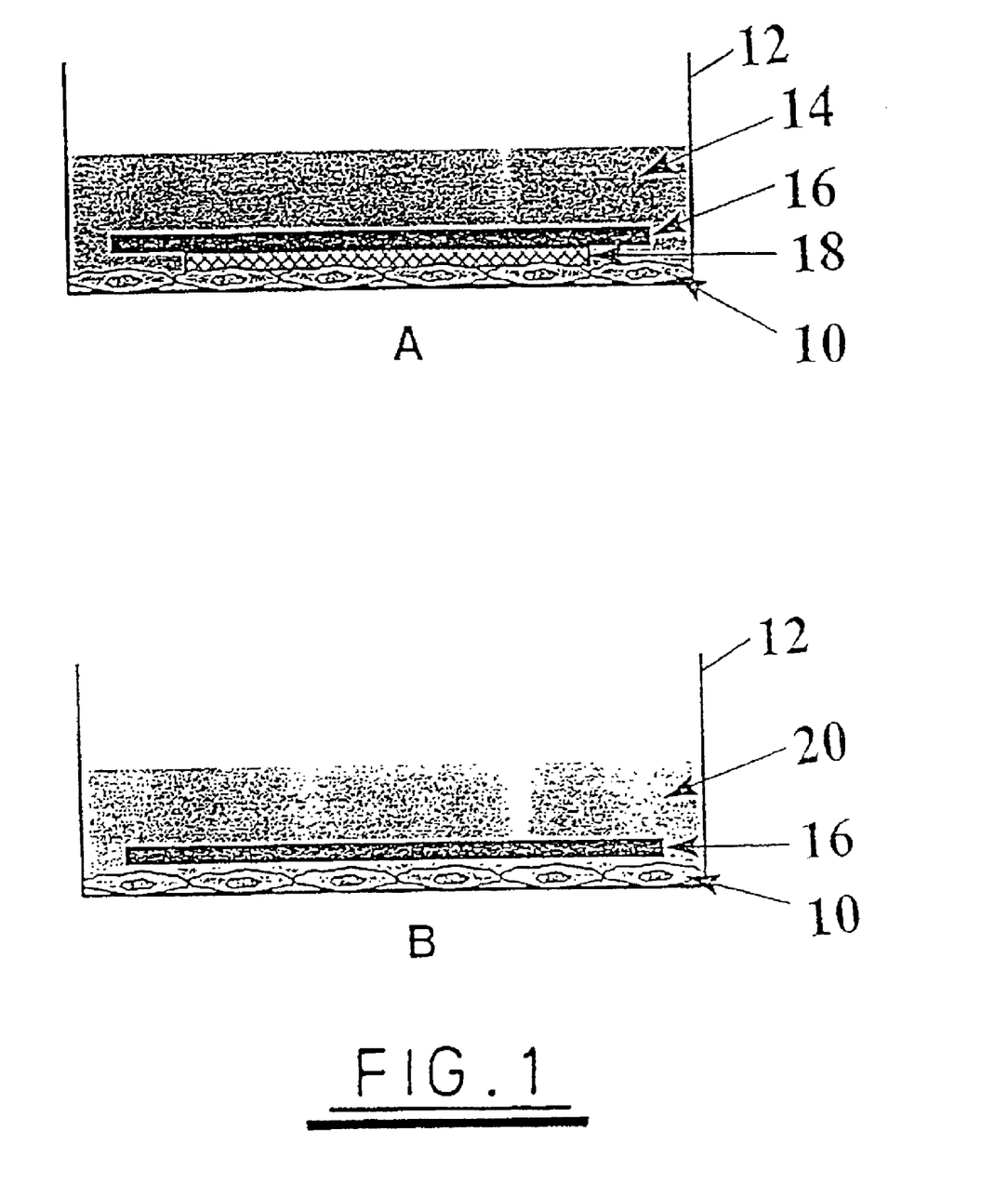
FIGS. 1A and 1B schematically represent the PAI/L assay of cryosections on coverslips (FIG. 1A) and coverslips alone (FIG. 1B) according to Example 1.

Referring to FIG. 1, the original PAI/L assay for the quantification of TGF-β in liquid samples was modified in order to measure active/latent TGF-β levels in a tissue section of a wound site to provide an indication of the levels at the wound site in vivo. As shown in FIG. 1A MLECs (10) were plated for 4 h into 24-well plates. one well (12) being represented in FIG. 1A ($3 \times 10^5$/ml, 500 μl/well) in complete DMEM and incubated for 4 hours at 37° C. Then, serum-containing medium was replaced with 500 μl of DMEM containing 0.1% pyrogen-poor BSA (from Pierce, Rockford, Ill., USA), aprotinin (1 μg/ml) (from Sigma, Dorset, UK) penicillin (100 U/ml) and streptomyciln (100 μg/ml), designated DMEM-BSA medium (14). The coverslips (16) carrying cryosections (18) were placed upside down onto the MLECs (10) in the 24-well plates.

As shown in FIG. 1B, to generate a TGF-β standard curve, MLECs (10) were incubated with serial dilutions of recombinant human TGF-β1 (0–250 pg/ml) (purchased from R & D Systems of Abingdon, Oxon, UK) in DMEM-BSA medium (20). These serial dilutions were added to the MLECs (10) together with methyl-cellulose coated coverslips (16).

Both samples and TGF-β standards were incubated with the MLECs (10) overnight at 37° C. MLECs (10) were then washed with phosphate buffered saline (PBS) and lysed with 200 μl of luciferase cell lysis buffer (from Analytical Luminescence Laboratory, Ann Arbor, USA) for 20 minutes at room temperature. Forty-five microliters of the lysates was transferred in triplicate to a Microlite 96-well plate (Dynatech Laboratories Inc. Chantilly, Va., USA). Luciferase activity in the lysates was determined using an MLX Microtiter Plate Luminometer (Dynex Technologies, Chantilly, Va., USA).

Example 2

Determining the Time for TGF-β Activation in Wound Healing

Wound tissue, surrounding tissue, and normal skin were embedded in methyl cellulose. Four cryosections (20 μm) representing four wounds of one animal were prepared onto duplicate coverslips and incubated overnight with MLECs. Twenty animals were used for this time course (two for each time point). MLECs were lysed and luciferase activity determined which was converted to TGF-β concentration (pg/mm$^3$) using a recombinant human TGF-β1 standard curve. The data represent mean values±SEM of 8 determinations.

Figure 2:
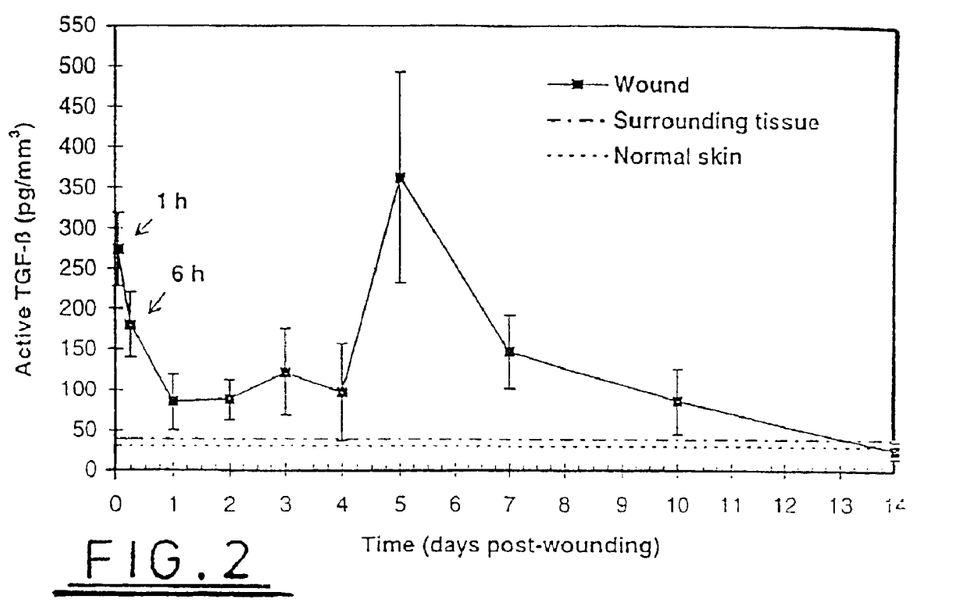
FIG. 2 shows a line graph illustrating the time course of active TGF-β generation in incisional wound repair according to Example 2.

In order to characterise latent TGF-β activation in wound repair, tissue samples were analysed at various time points post-wounding for active TGF-β in the PAI/L assay. Referring to FIG. 2 the average amounts of active TGF-β in normal skin and tissue surrounding the wounds were found to be 30 pg/mm$^3$ and 39 pg/mm$^3$, respectively. Since the detection limit of the assay is approximately 25–50 pg/mm$^3$, these levels are almost negligible. Immediately following wounding the tissue level of active TGF-β increased up to 9-fold (at 1 hour post-wounding). Active TGF-β levels declined within 24 hours but remained significantly higher than that in normal skin or surrounding tissue for 4 days post-wounding. A second major peak of active TGF-β was detected at 5 days post-wounding. By 14 days post-wounding, the level of active TGF-β had returned to that of normal skin. Although there was some variation in the absolute levels of active TGF-β between experiments, the kinetics and time points of the two peaks of growth factor activity were highly reproducible. Methyl cellulose used for tissue embedding did not significantly affect the assay.

Example 3

Determining the Ratios of TGF-β Isoforms in Wound Repair

Figure 3:
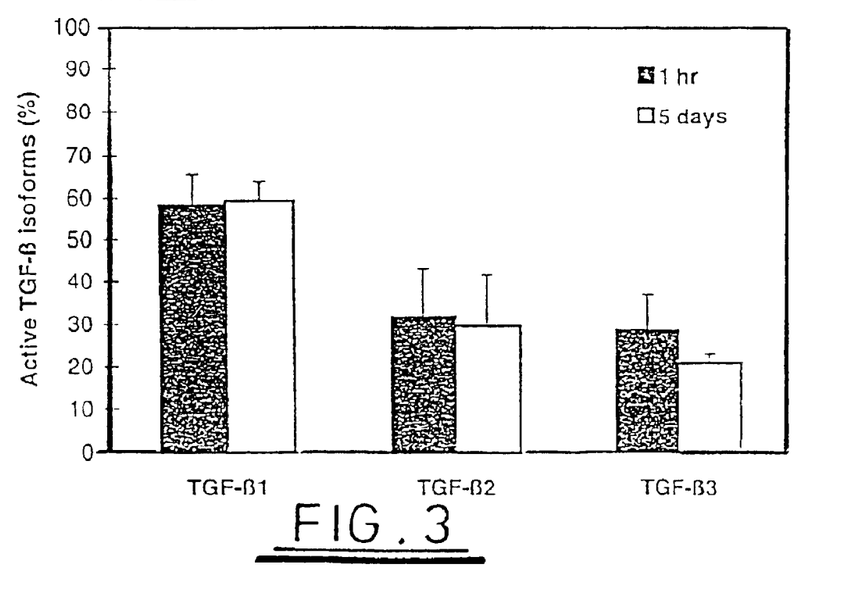
FIG. 3 shows a bar graph representing the isoforms of active TGF-β in wound tissue both 1 hour and 5 days post wounding according to Example 3.

The ratios of active TGF-β isoforms in the wound area were determined by assaying TGF-β activity in cryosections of wound tissue samples taken at the two peaktime points, 1 hour and 5 days post-wounding, in the presence of neutralising antibodies to TGF-β1, 2 and 3. The results shown in the bar graph of FIG. 3 represent mean values±SEM of 4 separate experiments. Four animals were used for each time point. The ratios of active TGF-β isoforms in the wound tissue samples were determined by addition of isoform-specific neutralising antibodies to TGF-β1, 2 and 3 to the PAI/L assay. The cryosections were pre-incubated with anti-TGF-β1, 2, and 3 antibodies (1 μg/ml, 5 μg/ml, and 5 μg/ml) (obtained from R & D Systems, Abingdon, Oxon, UK—AB-101-NA, AB-112-NA and AB-224-NA) for one hour at room temperature and then transferred onto the MLECs together with the antibody solution to measure residual TGF-β activity. Non-immune chicken IgY and goat IgG (obtained from Sigma, Dorset, UK) were used as controls.

Referring to FIG. 3 it can be seen that at both time points, TGF-β1 was the predominant isoform representing approximately 60% of the total active TGF-β. TGF-β2 accounted for 32% and 29% of TGF-β activity at 1 hr and 5 days post-wounding, and TGF-β3 for 28% and 21%, respectively. The combined inhibitory effect of all three isoform-specific antibodies exceeded 100%. This is probably due to the known cross-reactivity of the anti-TGF-β3 antibody used with TGF-β2 (50% cross-reactivity at the concentrations used, data not shown). Thus, the amount of TGF-β3 was significantly overestimated in these experiments. These observations indicate that the active TGF-β present in the wound area is predominantly TGF-β1 and 2.

Example 4

Determining the Total TGF-β in Wound Tissue

Figure 4:
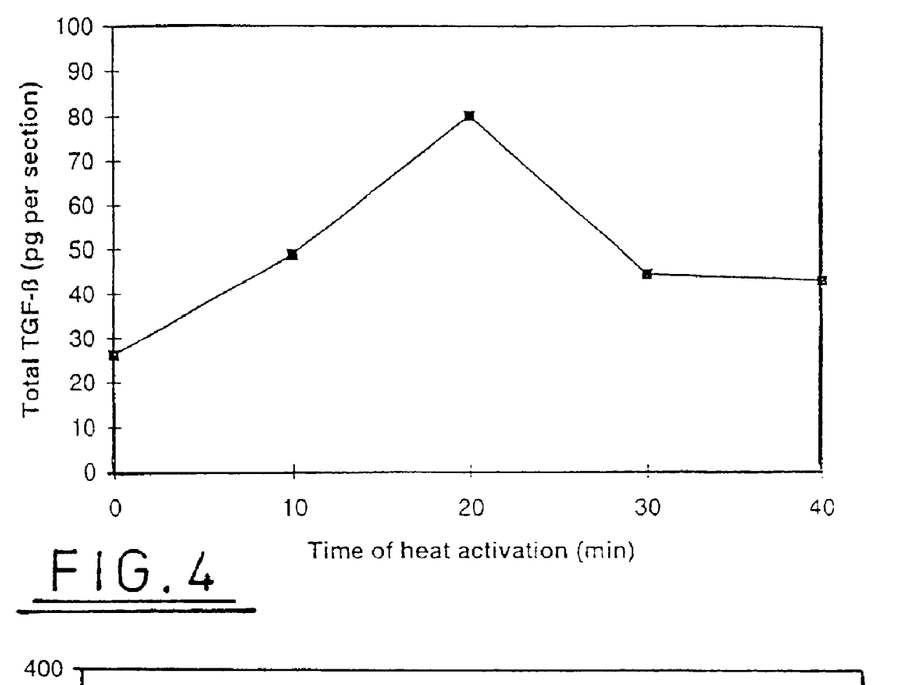
FIG. 4 shows a line graph illustrating the effect of heat activation of latent TGF-β in cryosections; according to Example 4.

In order to measure total TGF-β (active plus latent) in the wound tissue samples, the coverslips carrying the cryosections were submerged in 500 μl of DMEM-BSA medium in a sterile glass embryo dish (BDH, Merck, Leics., UK) and incubated for 20 minutes at 80° C. in order to heat activate latent TGF-β. Following heat activation, the coverslips were transferred, together with the medium, onto MLECs for TGF-β quantification in the PAI/L assay according to Example 1. Similar results were obtained in three separate experiments. As shown in FIG. 4 it was found that the optimal time period for heat activation of latent TGF-β in cryosections was 20 minutes.

Example 5

Elution of TGF-β from Cryosections

Since TGF-β was readily released into the medium during heat activation, how much of the active/total TGF-β could be eluted into the fluid phase prior to heat activation was determined and how much remained bound to the cryosections was determined. Cryosections taken from 1 hour and 5 day wounds were incubated with DMEM-BSA medium for 10 hours at 37° C. and the eluate assayed for both active and total TGF-β using the PAI-L assay described in Example 1. Four animals were used for each timepoint. The data are expressed as mean values±SEM of 3 separate experiments.

Figure 5:
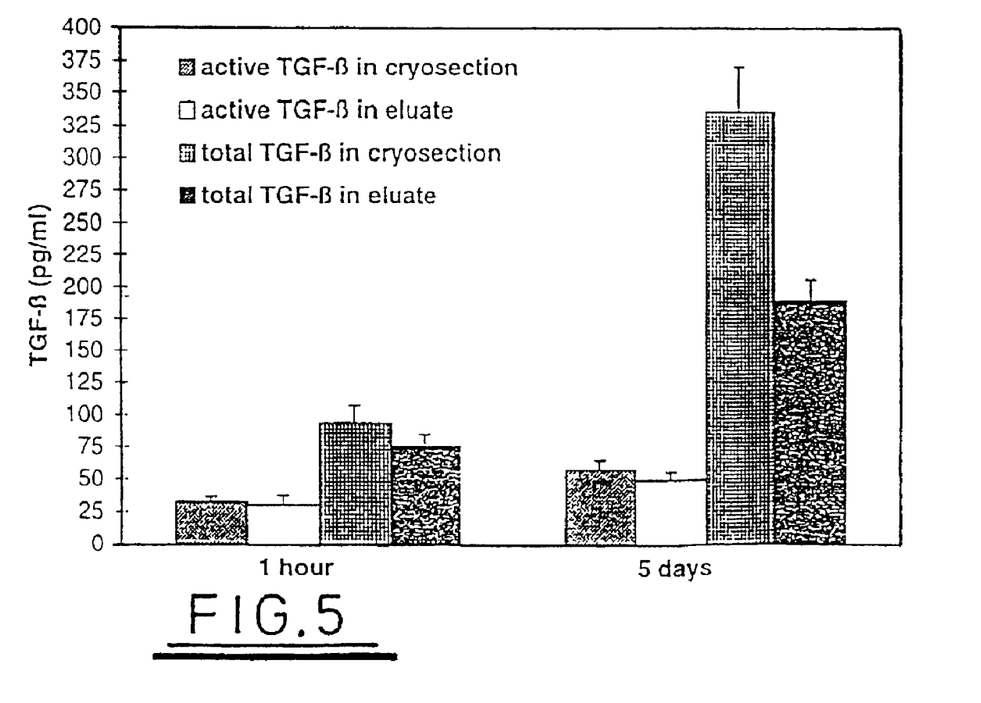
FIG. 5 illustrates the results of elution of active/total TGF-β from cryosections according to Example 5.

According to FIG. 5 the levels of active TGF-β in the eluate were similar to those in cryosections, indicating that virtually all active TGF-β detectable in the cryosections was released into the medium during incubation. In contrast, total TGF-β levels in the medium were lower than those in cryosections indicating that a significant portion of total TGF-β remained associated with the cryosections and could, therefore, only be determined following heat activation. Active TGF-β represented 38% of the total TGF-β at 1 hour and 17% at 5 days post-wounding, respectively. When cryosections and medium were analysed separately following heat activation, all the TGF-β activity was found in the medium and no remaining TGF-β was detected in the heated sections (data not shown). This indicates that all detectable TGF-β present in the cryosections had been released into the medium during heat activation.

Conclusions

Analysis of TGF-β action in vivo has previously not been possible because of the lack of quantitative methods to measure active and/or latent TGF-β in tissue. Therefore knowledge of changes of the amounts and types of TGF-β in vivo in response to stimuli, (for example during wound healing), has been based on in vitro assays whose results give an artificial indication of events in vivo. The modified PAI/L bioassay described in accordance with the present invention allows measurement of active/latent TGF-β isoforms in tissue sections and provides an accurate indication of events in vivo. The assay has been used to analyse TGF-β expression and activation in wound repair. Although some variation in the absolute values for active TGF-β present in wound tissue was observed between experiments, the time course of active TGF-β generation during wound repair was highly reproducible. TGF-βs are biologically active at picomolar concentrations and the PAI/L assay has a detection limit of approximately 10 pg/ml. In order to detect significant TGF-β activity in cryosections of wound tissue it was necessary to assay four wound sections on one coverslip. Since the total volume of four wound sections amounts to 0.1–0.2 mm$^3$, the detection limit for TGF-β in wound tissue in this assay was 25–50 pg/mm$^3$.

Latent TGF-β is produced by a number of cell types involved in wound repair including platelets, macrophages, fibroblasts, endothelial cells and keratinocytes. However, amounts and isoforms of latent TGF-β that are activated following wounding have not previously been determined. Using the assay in accordance with the present invention it was found that significant amounts (up to 274 pg/mm$^3$) of latent TGF-β are activated immediately following wounding. We believe this may be due, at least in part, to latent TGF-β activation initiated during fibrin clot formation. Platelets represent the most concentrated source of latent TGF-β1. Following wounding platelets immediately accumulate at the site of wounding, and latent TGF-β1 stored in platelet α-granules is released into the wound area. Thus, platelet-derived TGF-β1 might be one of the major sources of active TGF-β generated at early time points following wounding. This pool of active TGF-β1 might be involved in initiating early inflammatory responses through its chemotactic effects on neutrophils and monocytes.

TGF-β2 is present mainly in body fluids such as amniotic fluid, saliva, milk, and the aqueous and vitreous of the eye. TGF-β2 is also predominant in foetal wound fluid. However, since we have found TGF-β2 is not present in the circulation (unpublished data), the cellular source of TGF-β2 at the wound site is presently unknown. The rapid decline of TGF-β activity observed at day 1 post-wounding may be due to the uptake and inhibition of TGF-β by cells. It may also result from diffusion of platelet-derived TGF-β out of the wound area or degradation by proteases.

During wound healing, several cell types including macrophages, fibroblasts, keratinocytes, and endothelial cells migrate from the surrounding tissue into the wound area, and all of them may produce and activate TGF-βs. TGF-β isoforms produced and activated by these cells may contribute to the second peak of TGF-β activity occurring during wound repair. Alternatively and additionally, the second peak of TGF-β activity might be due to the release of pre-existing active or latent TGF-β from pools of soluble or extracellular matrix TGF-β binding proteins including $\alpha_2$-macroglobulin, latent TGF-β binding proteins (LTBPs), biglycan, decorin, fibromodulin, lumican, betaglycan, fibronectin, type IV collagen, and thrombospondin. Interaction with these binding proteins may protect TGF-βs from degradation and provide long-term reservoirs of active or latent growth factor. When needed, TGF-βs may be mobilised from these reservoirs and released into the wound area to act on target cells. For example, latent TGF-βs can be incorporated into the extracellular matrix via LTBP-1, which can be released from the matrix and activated by proteases such as plasmin, thrombin, mast cell chymase and leukocyte elastase. In addition, it has been suggested that small latent TGF-β1 complex released from platelets is retained in the fibrin clot through binding to the platelet surface receptor, glycoprotein IIb/IIIa. This TGF-$\beta_1$ can be released into the wound area in an active form when the fibrin clot is dissolved by plasmin. This mechanism of active TGF-β generation may also contribute to the second peak observed at day 5 post-wounding. The main functions of TGF-β at this stage of wound repair include stimulation of fibroblast migration, induction of angiogenesis, and increase in granulation tissue formation.

The ratio of active versus total TGF-β determined using the assay according to the present invention in dermal wound healing is relatively high compared to those reported for latent TGF-β activation in cell culture systems. It was found that 38% of the total TGF-β is active at 1 hour post-wounding and 17% at 5 days. It has been reported that active TGF-β accounted for only 1% of the total TGF-β in conditioned medium from co-cultures of bovine endothelial cells and pericytes or smooth muscle cells Similarly, retinoic-acid treated bovine endothelial cells activate 3–5% and LPS-stimulated peritoneal macrophages 8% of the latent TGF-β present in conditioned medium. Results from assays carried out in accordance with the present invention suggest that there is a significant difference in the apparent efficiency of latent TGF-β activation in wound repair in vivo compared to that in cell culture models in vitro. This might be explained by suboptimal activation conditions in in vitro models.

The pool of active TGF-β measured in wound tissue using the assay in accordance with the present invention appears to be in the fluid phase since it can be eluted from cryosections. Although the majority of latent TGF-β was also eluted into the medium, a significant portion of it was retained in the cryosections suggesting that latent TGF-β may be cross-linked to extracellular matrix proteins via LTBPs. It was determined that mature TGF-β could be released from this pool by heat activation.

Since TGF-β1, 2 and 3 have been shown to have distinct functions in wound healing and scarring the ratios of active TGF-β isoforms at the early (one hour postwounding) and late stage (five days postwounding) of wound repair were determined. TGF-β1 and 2 were identified in wound tissue at both time points with TGF-β1 being the predominant isoform. Although a significant fraction (30%) of TGF-β activity was neutralised by anti-TGF-β3 antibodies, a considerable proportion of this inhibition (estimated half of it) was probably due to cross-reactivity of the antibodies with TGF-β2. Thus, the proportion of active TGF-β3 in wound tissue appears to be relatively small (approximately 13% and 6% at 1 hour and 5 days post-wounding, respectively). It is suggested that the assay may be optimised by use of a more specific Anti-TGF-$\beta_1$ antibody. These results are consistent with a previous report indicating that more than 85% of TGF-β in adult wound fluid is TGF-β1 (Longaker et al., "Wound healing in the foetus: Possible role for inflammatory macrophages and transforming growth factor β isoforms" Wound Rep. Reg. 2: 104–112, 1994). The assay results are also in agreement with the in vivo wound healing studies performed by Shah et al. 1992, supra and Shah et al., "Neutralising antibody to TGF-β1,2 reduces cutaneous scarring in adult rodents" J. Cell Sci. 107: 1137–57, 1994). They have shown that injection of neutralising antibodies to TGF-β1 and 2 into adult rat incisional wounds at early time points post-wounding reduces scarring. As demonstrated in this study, the predominant isoforms of active TGF-β in adult wounds during early stages of wound repair are TGF-β1 and 2.

Since latent TGF-β activation is considered to be a key point in the regulation of TGF-β action, recent studies have focused on the modulation of latent TGF-β activation in vivo in order to improve the quality of wound repair and scarring. It has been shown that application of mannose 6-phosphate or transglutaminase inhibitors into rat dermal wounds improve the quality of scarring. Since both latent TGF-β binding to the mannose 6-phosphate receptor as well as transglutaminase activity are required for latent TGF-β activation in certain cell culture systems' previous assays suggested that the reduction in scar formation may be due to an inhibition of the activation of latent TGF-β1 and/or 2. However, due to the lack of a quantitative assay for active TGF-β in vivo, this hypothesis could not be tested. The assay in accordance with the present invention now allows the monitoring of latent TGF-β activation as occurs in vivo and may be employed to further investigate the mechanisms by which mannose 6-phosphate and transglutaminase inhibitors modulate wound repair and scarring (as illustrated by Examples 6 and 7 below).

Example 6

In vivo Levels of Active and Total TGF-β in Animals Treated with mannose-6-phosphate.

Studies have demonstrated that reduction of active TGF-$\beta_{1+2}$ at the wound site results in a reduction in scarring. TGF-β's are secreted as biologically inactive complexes with a glycosylated latency associated peptide (LAP), where M6P occurs in two of the three oligosaccharide side chains of the LAP. Binding of the LAP to the M6P/IGF II receptor is a critical step in latent TGF-β activation. We have previously demonstrated that local administration of M6P significantly reduces scarring in a rat incisional wound model, but have not shown that this is due to the reduction of the in vivo levels of active TGF-β. We therefore designed experiments to measure active and total TGF-β levels in M6P treated wounds. These studies will (i) establish the mechanism for the anti-scarring effect of M6P, (ii) allow the optimisation of M6P therapy, and (iii) provide a screening assay for anti-scarring compounds.

Methods 20 animals each received 4 wounds which were subsequently treated with M6P (100 mM, 100 µl/wound/day). Animals were killed at 1 and 6 hours and 1, 3, 5, 7, 10 and 14 days post wounding. The wounds were dissected and embedded in methyl cellulose, then snap frozen. The tissue samples were subsequently prepared for use in the modified PAI-1/L assay.

Results

Figure 6:
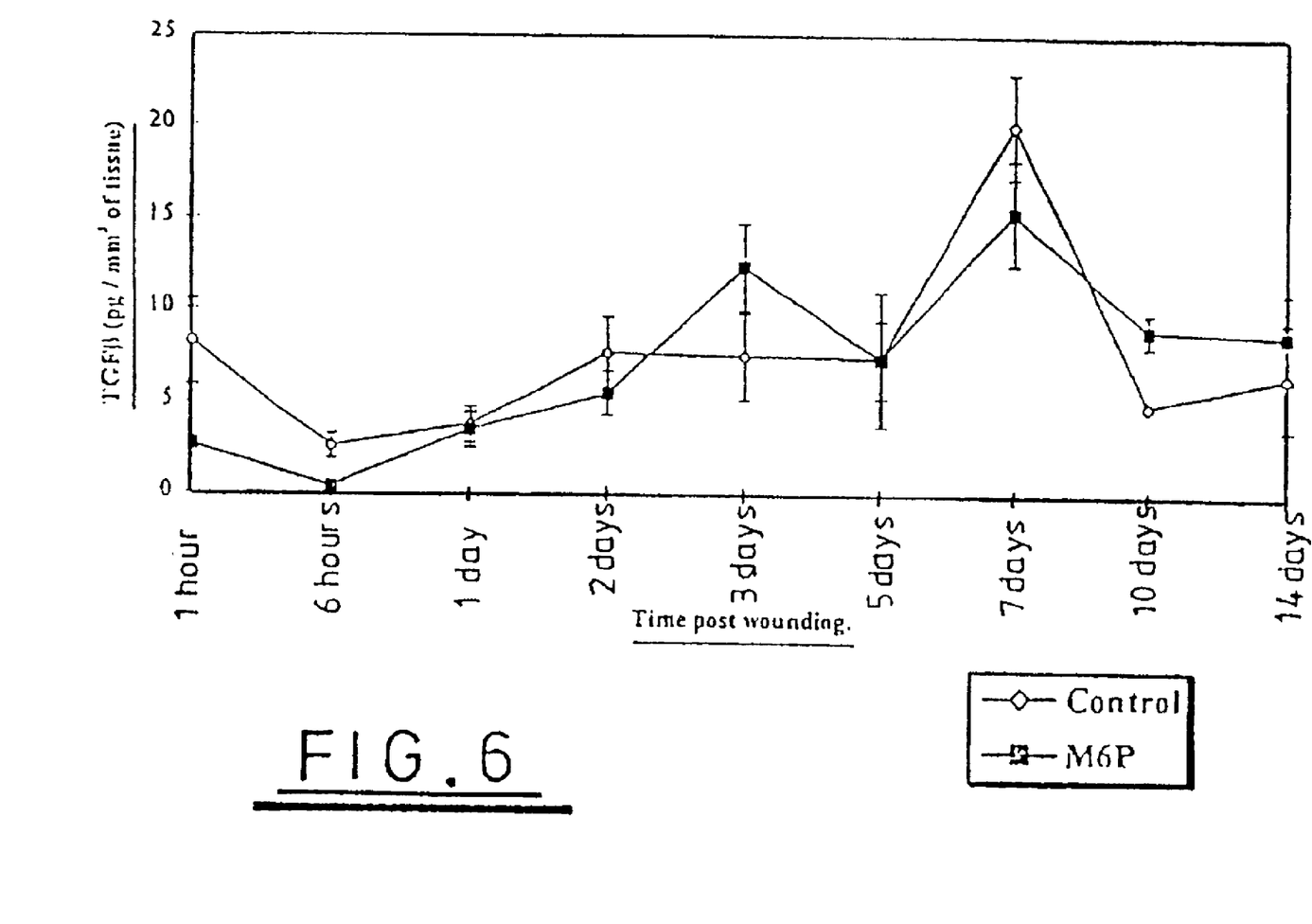
FIG. 6 illustrates active TGF-β in wound sections from control and M6P treated animals according to Example 6.

The level of active TGF-β in M6P treated wounds was less at 1 and 6 hours post wounding when compared with PBS controls. After this time the levels are comparable until 10 days post wounding, when M6P treated wounds have more active TGF-β than controls (FIG. 6).

Figure 7:
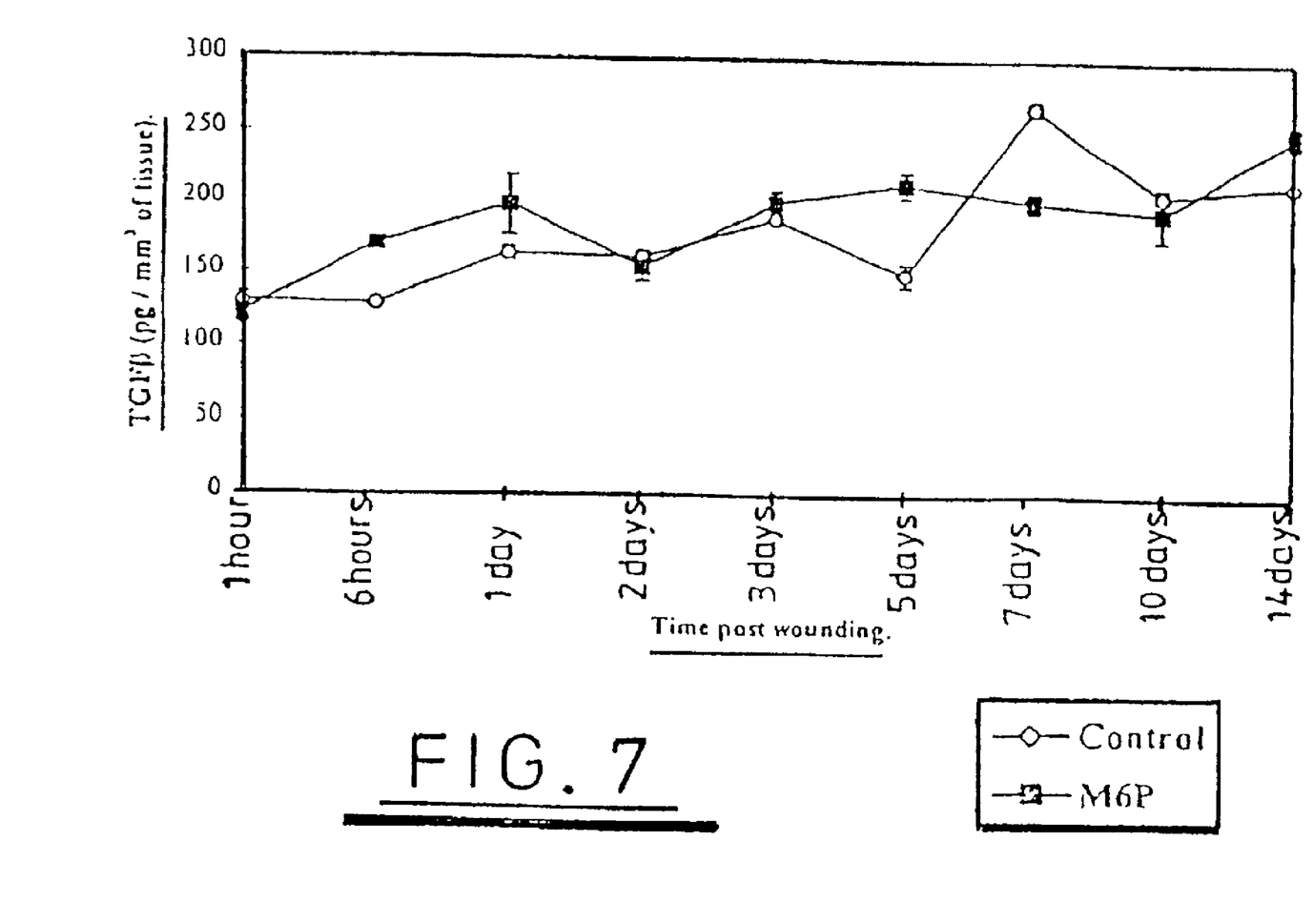
FIG. 7 illustrates total TGF-β in wound sections from control and M6P treated animals according to Example 6.

The level of total TGF-β in M6P treated wounds was similar to those of control wounds, except at 6 hours, 5 days and 10 days post wounding (higher than controls) and 7 days post wounding (less than controls). See FIG. 7.

Taken together, these data suggest that M6P is effective in reducing the levels of active TGF-β in vivo. This does not appear to be due to decreased secretion of latent TGF-β, but probably due to decreased activation of the latent form. The results confirm that M6P acts at the early stages of wound repair to improve wound healing/scarring.

Example 7

Prevention of Latent TGF-β Activation by Transglutaminase Inhibitors

Transglutaminases have been implicated in the process of TGF-β activation. Therefore inhibitors of these enzymes may be useful for reducing the levels of active TGF-β following injury and hence prevent scarring. Thus the method according to the invention was used to evaluate in-vivo TGF-β activity in the presence or absence of a Transglutaminase inhibitor.

Briefly, rat incisional wounds were treated with 1 mM monodansylcadaverine (MDC), a potent inhibitor of Transglutaminase activity. The wounds were prepared and assayed as described previously.

Figure 8:
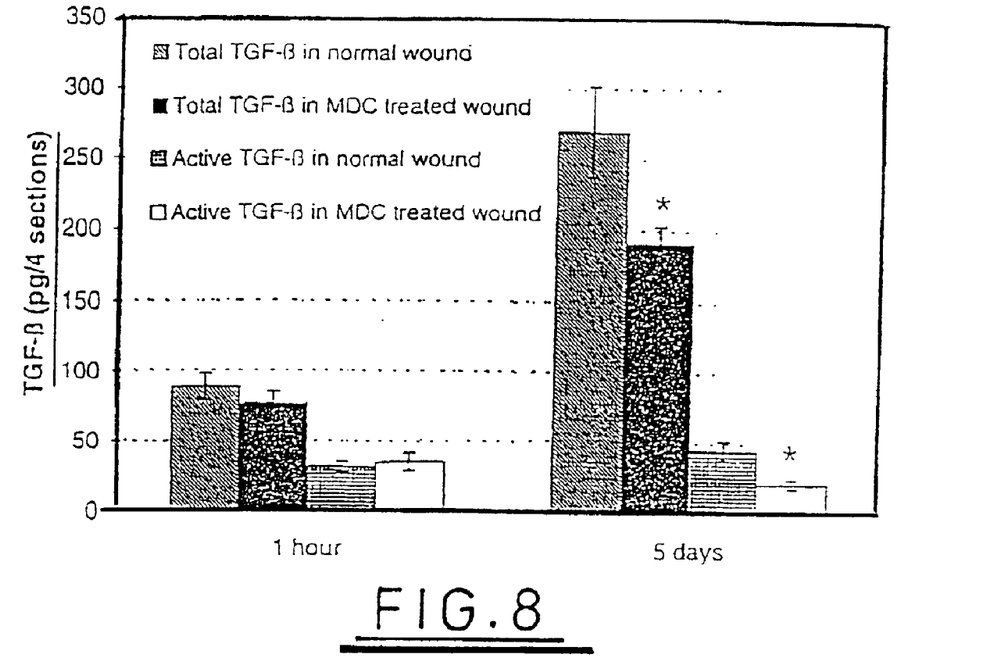
FIG. 8 illustrates that MDC inhibits TGF-β activation in vivo according to Example 7.

MDC at this treatment regime improves scarring and reduces early TGF-β levels. This confirms previous emperical data which suggested the need to give MDC therapies immediately post wounding for best antiscarring effect. The data presented in FIG. 8 demonstrates that MDC, inhibits TGF-β activation in vivo.

Example 8

The Effects of Kistrin on Latent TGF-β Binding to the Fibrin Clot

Work was also carried out to investigate the effect of kistrin on TGF-β activity.

Kistrin is a compound (a disintegrin) which is thought to prevent latent TGF-β from binding to the fibrin clot, although it has not been possible to test this hypothesis in vivo until now. Since the clot may provide a source of TGF-β during the course of healing, inhibition of this process may help to reduce the subsequent release of active TGF-β.

Briefly, rat incisional wounds were treated with 100 µM kistrin, then prepared and assayed as described previously.

Figure 9:
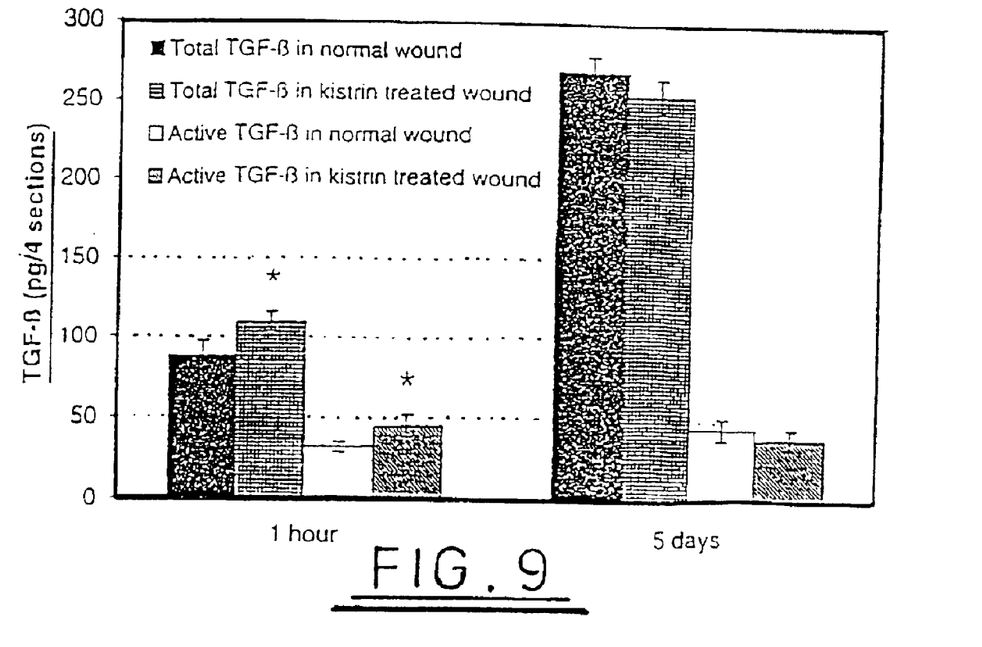
FIG. 9 illustrates the affect of kistrin and total and active TGF-β according to Example 8.

The results are presented in FIG. 9 and show at 1 hour post wounding that the levels of both active and total TGF-β are increased in kistrin treated wounds when they are compared to controls However, there was no difference in the amount of latent TGF-β. There were no differences at 5 days post wounding. These data are interesting as kistrin has no antiscarring effect—if anything the wounds are worse. This correlates with the higher levels of active TGF-β at 1 hour post wounding.

Example 9

In Vivo Levels of Active and Total TGF-β in Plasminogen Knockout Mice

Tissue from transgenic mice deficient in plasminogen was used to demonstrate that the method according to the present invention had utility for testing tissue from a genetically modified animal model. Since plasmin plays a key role in the TGF-β activation pathway we investigated whether these animals retain the ability to activate TGF-β in vivo.

Methods 22 animals were wounded: 13 knockouts (KO) and 9 wild types (WT), and killed at 1 hour or 5 days post wounding. The wounds were dissected and embedded in methyl cellulose, then snap frozen. The tissue samples were subsequently prepared for use in the PAI-1L assay.

Results

Figure 10:
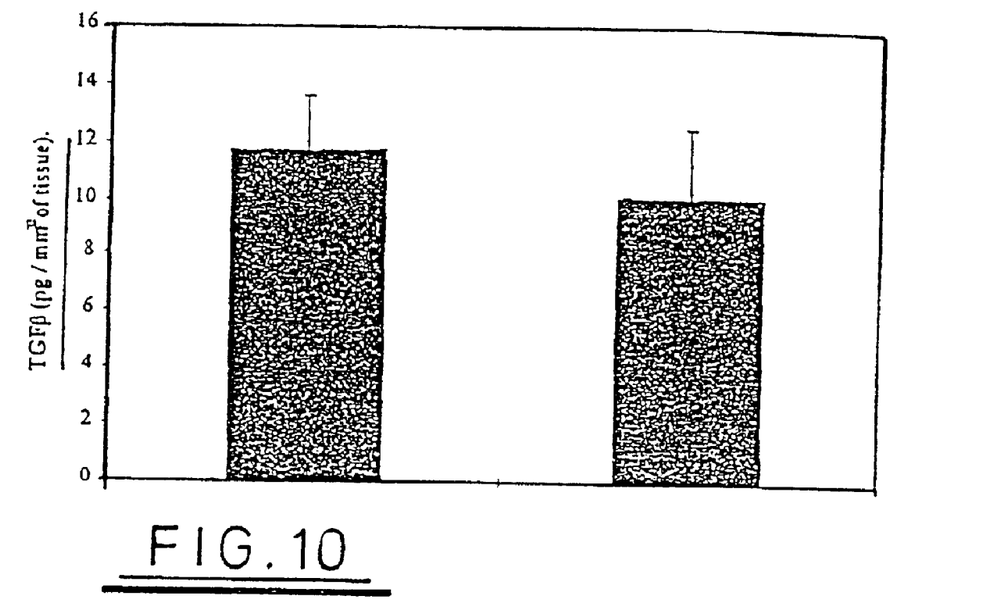
FIG. 10 illustrates active TGF-β in sections from knockout wounds and wild type wounds according to Example 9.
Figure 11:
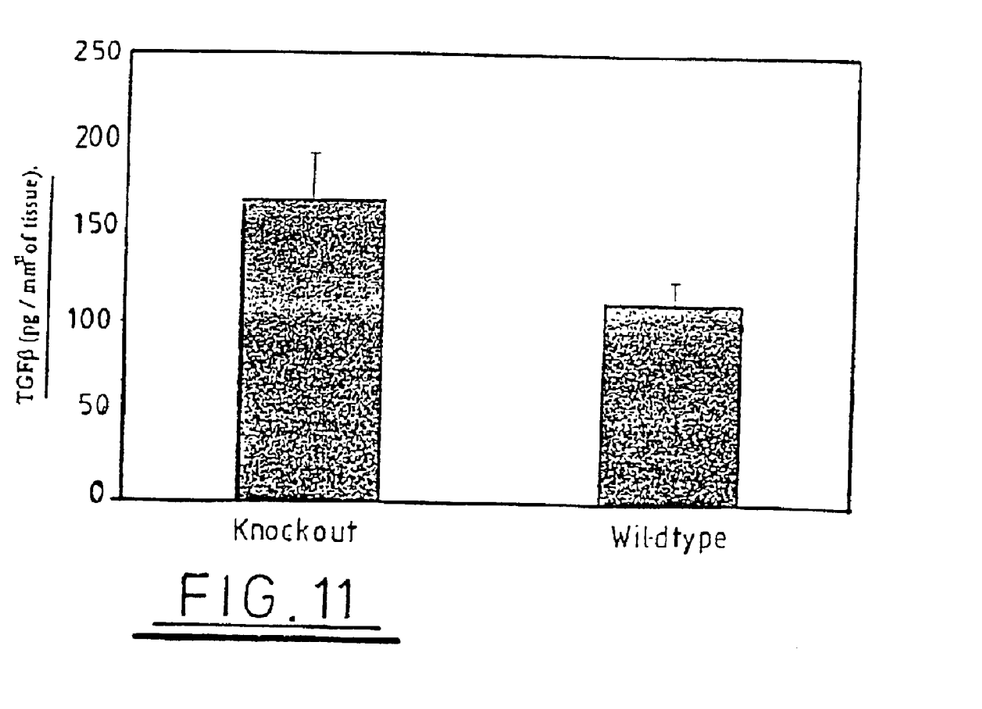
FIG. 11 illustrates total TGF-β in sections for knockout wounds and wild type wounds according to Example 9.

The levels of active TGF-β were very similar when KO animals were compared with WT littermates (FIG. 10). Plasminogen deficient animals had consistently lower levels of total TGF-β (FIG. 11) when compared with WT littermates.

The assay method according to the present invention allows for quantitative determination of TGF-β levels in vivo, the assay result providing an accurate reflection of events in the tissue. The assay will have utility in monitoring latent TGF-β activation in a system that reflects in vivo conditions, allowing proposed modulators of TGF-β activation to be tested with some degree of accuracy. TGF-β present in tissues may be an important prognostic and therapeutic marker in certain conditions. Therefore, being able to effectively measure the likely levels of active TGF-β isoforms in a particular tissue by the assay described herein may contribute to improved strategies for prognosis and/or post-operative treatment for pathological conditions in which TGF-β plays important roles, for example wound repair, fibrosis and cancer development.

What is claimed is:

1. An assay for quantifying the amount of active transforming growth factor β (TGF-β) in a sample, the TGF-β assay comprising:
   (a) incubating the sample together with eukaryotic cells which contain a TGF-β responsive expression vector having a structural region encoding an indicator protein for a predetermined time period sufficient for said eukaryotic cells to express a detectable amount of said indicator protein;
   (b) measuring the amount of said indicator protein expressed during said time period; and
   (c) determining the amount of TGF-β present in the sample by comparing the measured amount of said indicator protein against reference data;
wherein the sample comprises a cryosection of a tissue, said cryosection having been treated such that said TGF-β is in an active and/or latent form.

2. The assay according to claim 1, in which the reference data represents a series of measured amounts of said indicator protein produced from a series of known concentrations of TGF-β by the eukaryotic cells.

3. The assay according to claim 1, in which the indicator protein is luciferase.

4. The assay according to claim 1, in which the cryosection is prepared by dissecting extracts of tissue and embedding them in a support before snap freezing the tissue in liquid nitrogen.

5. The assay according to claim 4, in which the support is methyl cellulose.

6. The assay according to claim 1, in which the cryosection is up to 50 μm thick.

7. The assay method according to claim 6, in which the cryosection is less than 30 μm thick.

8. The assay according to claim 6, in which the cryosection is substantially 20 μm thick.

9. The assay according to claim 1, in which the cryosection is mounted on a coverslip.

10. The assay according to claim 9, in which each coverslip carries more than one cryosection.

11. The assay according to claim 9, in which a single coverslip carries up to four cryosections.

12. The assay according to claim 1, in which the concentration of TGF-β is determined by dividing the amount determined by the assay by the volume of the sample, whereby the volume of the sample is determined by multiplying the thickness of the sample by the area of the sample and whereby the area of each cryosection sample is determined by staining and imaging.

13. The assay according to claim 12, in which staining is by haematoxylin and eosin.

14. The assay according to claim 9, in which the cryosection is incubated with the eukaryotic cells containing a TGF-β responsive vector by inverting the coverslip carrying one or more cryosections and placing the coverslip over the eukaryotic cell culture such that the or each cryosection contacts the eukaryotic cells.

15. The assay according to claim 1, carried out on both test samples and control samples to indicate TGF-β levels in vivo.

16. The assay for determining the levels of TGF-β isoforms in a sample, comprising the assay according to claim 1, preceded by the step of preincubating the cryosections with anti-TGF-β isoform neutralising antibodies for a predetermined length of time.

17. The assay for determining the total amount of TGF-β (both latent and active) in a sample, comprising the assay according to claim 1, preceded by a heat activation step in which the cryosections are heated to about 80° C. for a predetermined time.

18. An assay for determining the ratio of active to total TGF-β levels in a sample, comprising first carrying out the assay method according to claim 1 and then heat treating the same cryosections as used in that first assay and then repeating the assay according to claim 1.

* * * * *